United States Patent [19]

Moore

[11] Patent Number: 5,597,840
[45] Date of Patent: Jan. 28, 1997

[54] MICROEMULSION FORMULATION FOR INJECTION INTO TREES

[75] Inventor: Carolyn E. Moore, Kernersville, N.C.

[73] Assignee: Ciba-Geigy Corporation, Tarrytown, N.Y.

[21] Appl. No.: 271,809

[22] Filed: Jul. 7, 1994

[51] Int. Cl.$^6$ .................................................. A01N 25/02
[52] U.S. Cl. .................... 514/365; 514/383; 514/376; 514/395; 514/478; 514/625
[58] Field of Search ................................ 514/383, 365, 514/376, 395, 478, 625

[56] References Cited

U.S. PATENT DOCUMENTS

| | | | |
|---|---|---|---|
| 3,266,980 | 8/1966 | Newcomer et al. | 514/646 |
| 4,989,366 | 2/1991 | DeVlieger | 47/57.5 |
| 5,037,653 | 8/1991 | Dawson | 424/405 |
| 5,093,326 | 3/1992 | Herman | 514/172 |
| 5,249,391 | 10/1993 | Rodgers | 47/57.5 |
| 5,395,942 | 3/1995 | Worthington | 548/268.8 |

OTHER PUBLICATIONS

Appel, "Intravascular injection with propiconazole in live oak for wilt control", Plant Disease, 1992, 76(11), 1120–1124.

*Primary Examiner*—Brian M. Burn
*Assistant Examiner*—Brian G. Bembenick
*Attorney, Agent, or Firm*—Marla J. Mathias; William A. Teoli, Jr.

[57] ABSTRACT

An agrochemical microemulsion composition for injection into trees, and the use of said composition for preventing and treating damage to trees from disease and pests or regulating tree growth. The composition includes a nonpolar agrochemical active ingredient, a water-miscible solvent, and an emulsifying agent. When the composition is diluted in water, the particle size of the active ingredient is between about 0.01 and about 0.1 microns.

11 Claims, No Drawings

MICROEMULSION FORMULATION FOR INJECTION INTO TREES

BACKGROUND OF THE INVENTION

The present invention relates to an agrochemical composition for injection into trees. More particularly, the invention relates to a microemulsion formulation.

The application of agrochemicals such as fungicides, insecticides or plant growth regulators directly to trees through injection is known in the art. U.S. Pat. No. 3,266,980 describes a trichlorophenylacetamide compound for use against vascular tree diseases caused by microorganisms, and lists several methods of application to trees, including injection as a solution into the trunk or root zone. Similarly, U.S. Pat. No. 5,093,326 describes trioxacyclopentane compositions for use against insect infestations and plant diseases, and lists injection into trees as one preferred method of application.

The use of macroemulsion fungicidal formulations against tree disease is also known in the art. These formulations may be applied through tree injectors, which typically involves pouring the macroemulsion composition, over a period of time, through tubing into a hole pre-drilled into the tree. An example of such a macroemulsion formulation is the fungicidal composition BANNER® (Ciba-Geigy Corporation, Ardsley, N.Y.).

Finally, microemulsion formulations and injectors are also known in the art. Typically, microemulsion formulations are distinguished from pure solutions and macroemulsion formulations in that the particle size of the active ingredient suspended in the formulation is approximately 0.01–0.1 g in size. An example of such a microemulsion formulation is the fungicidal composition FUNGISOL® (J. J. Mauget Company, Los Angeles).

It has now been found that a microemulsion agrochemical composition containing a nonpolar agrochemical active ingredient, a water-miscible solvent, and an emulsifying agent, has several advantages over known formulations. This composition requires little or no dilution, minimizes damage to the tree, requires no agitation for homogeneity, and is absorbed quickly into the tree.

DESCRIPTION OF THE PREFERRED EMBODIMENTS

The agrochemical compositions of the present invention include a nonpolar agrochemical active ingredient, a water-miscible solvent, and an emulsifying agent. The compositions are microemulsions, i.e. when the composition is diluted in water, the average particle size of the active ingredient is between about 0.01 and about 0.1 microns.

The active ingredient is non-polar. If a polar active ingredient is used in conjunction with the invention, the composition will form a true solution and not form the correct particle size upon dilution. Examples of non-polar active ingredients include, but are not limited to, non-polar fungicides, non-polar insecticides (including insect growth regulators), and non-polar plant growth regulators.

Examples of non-polar fungicides include, but are not limited to, non-polar triazoles such as propiconazole, hexaconazole and triadimefon, non-polar carbamates such as benoymyl and thiophanate-methyl, non-polar acetanilides such as metalaxyl and oxadixyl, and non-polar imidazoles such as thiabendazole and carbendazim.

Examples of non-polar insecticides and insect growth regulators include non-polar organophosphates such as diazinon, malathion, dimethoate and chlorpyrifos, non-polar triazines such as cyromazine, non-polar benzoylureas such as diflubenzuron and pyrmetrozine, non-polar carbamates such as fenoxycarb, carbofuran and carbaryl, and non-polar pyrethroids such as cypermethrin and permethrin.

Examples of non-polar plant growth regulators include non-polar carboxylates such as trinexapac-ethyl, non-polar triazoles such as paclobutrazol, and non-polar pyrimidines such as fluprimidol.

The amount of active ingredient present in the concentrated composition should ideally be as high as possible without crystallizing. The amount of active ingredient present in the final composition applied to the tree (whether diluted or not) should be as high as possible while still affording good tree compatibility.

The water-miscible solvent is necessary to form the microemulsion in conjuction with the nonpolar active ingredient. If the solvent is not water-miscible, the composition will be more prone to form a macroemulsion. The water-miscible solvent is preferably selected from the group consisting of alcohols such as 1-butanol, 2-butanol, tetrahydrofurfuryl alcohol and methanol, ketones such as acetone, glycerine, glycols such as propylene glycol, glycol ethers such as propylene glycol monoethyl ether, and heterocyclic compounds such as $\gamma$-butyrolactone and n-methyl pyrrolidone.

The water-miscible solvent is preferably present in an amount between about 0.5 to about 5 parts by weight per part active ingredient, and most preferably present in an amount of about 3 parts by weight per part active ingredient. The optimal amount of solvent will be dependent upon the particular ingredients used in the composition.

The emulsifying agent is required to form a microemulsion. Preferred emulsifying agents include alkoxylated alkyl amines, alkoxylated alkyl phenols, alkylphenyl sulfonate, alkylphenyl sulfonate metal salts, alkylphenyl sulfonate amine salts, dialkyl sulfosuccinates, akoxylated natural oils, tetraalkyl ammonium salts, polyoxyalkylene copolymers, alkylated polyglycosides, alkylated saccharides and polysaccharides such as sorbitan.

The emulsifying agent is preferably present in an amount between about 0.2 to about 3 parts by weight per part active ingredient, and most preferably present in an amount of about 2 parts by weight per part active ingredient. The optimal amount of emulsifying agent will be dependent upon the particular ingredients used in the composition, and should be enough to form a microemulsion.

The composition may include additional inert ingredients. Water may be added if necessary to make the composition less toxic or less viscous. Dyes may be included for safety or other considerations. Bitter-tasting agents such as denatonium benzoate (BITREX®) may be used to protect against accidental ingestion by children or animals.

The fungicidal and plant growth regulating formulations in accordance with this invention are intended to be used with various types of deciduous trees, including, but not limited to, oak, elm, ornamental prunist species such as cherry, plum, pear, crab apple and peach, crepemyrtle, holly, maple, sycamore, birch, beech and aspen. The insecticidal formulations in accordance with this invention are intended to be used with not only deciduous trees such as those listed above, but also conifer trees.

Tree diseases which are contemplated to be treated or prevented in accordance with this invention include, but are not limited to, oak wilt, dutch elm, scab diseases, powdery mildew, rust disease and leaf spot.

The insecticidal formulations in accordance with this invention are intended to be used against a variety of insects and other arthropods, including but not limited to lepidoptera such as gypsy moth, web worms, loopers, leaf rollers, bag worms, leaf miners and tent caterpillars; coleoptera such as japanese beetle and other leaf beetles; tree feeders such as borer beetles and bark beetles; diptera such as leaf miners; and hymenoptera such as saw flies. Other arthropods include arachnids such as mites.

The formulations in accordance with this invention are particularly effective for use in microinjection into the root flare area of the tree. The root flare area is the transitional zone between the trunk and the root system. Uptake and distribution of the formulation is more effective when injections are made into the flare roots. In addition, wounds created in the root flare area close more rapidly in comparison to wounds above the root flare area.

The diameter of the tree is preferably measured using a tree diameter tape (D tape) at 4½ ft. above the ground. This is the diameter at breast height (DBH). The DBH measurement is used to determine the amount of formulation needed to inject into the tree.

Heavy, thick or loose outer bark is carefully shaved to form a smoother injection point and to ensure the operator that the drill hole penetrates through the bark to the xylem. If root flares are not clearly exposed, 2–4 inches of soil should be carefully removed from the base of the tree to uncover the top of the root flares. Loose soil is preferably brushed away.

Microinjection units are preferably spaced no further than 5 inches apart. A slight downward angle hole is recommended for more complete drainage of the microinjection unit.

The formulation may be injected into the tree using any known injection techniques. However, the preferred microinjection procedure is as follows:

Using an electric drill at 600 to 800 rpm, with a sharp, clean 11/64 inch (0.4 cm) drill bit, the installer should drill evenly spaced holes to a depth of ⅜–½ inch (0.90–1.3 cm) through the bark into the xylem. After reaching the proper depth range, the drill bit should be withdrawn carefully to avoid dislodging bark fragments around the exterior opening of the hole.

The drill bit should be disinfected between trees with a cleaner or 20% solution of household bleach. The bit should be rinsed after treatment with cleaner or bleach.

Each hole should be drilled and a microinjection unit installed as soon as possible after the hole is drilled. A small amount of water squirted into the drill hole will help form a tight seal. Special cartridges containing a predetermined amount of the formulation are placed in the hole, and the formulation contained therein is dispensed into the tree over a period of several minutes.

Examples of tree injection devices suitable for use with this invention are disclosed in U.S. Pat. Nos. 4,989,366 and 5,249,391.

The formulations in accordance with the invention may also be diluted and applied to the tree using known macroinjection techniques. In general, these techniques involve the drilling of holes as in the microinjection technique, and then the application of dilute formulation through plastic tubing inserted into the holes.

Whether injected with macro or micro injection techniques, the formulations in accordance with the invention are less phytotoxic than macroemulsion formulations, and do not require dilution. Additionally, they are absorbed much more quickly into the tree, and do not require agitation to remain homogeneous.

The following examples are intended for illustrative purposes only, and are not intended in any way to limit the scope of the invention.

EXAMPLE 1

A microemulsion concentrate formulation has the following ingredients:

| Ingredient | % by weight |
| --- | --- |
| Propiconazole Technical (91.7% active ingredient) | 15.59 |
| Tetrahydrofurfuryl Alcohol | 46.408 |
| Ethoxylated Castor Oil (36–40 moles ethylene oxide) | 29.5 |
| Distilled Water | 8.4 |
| FD&C Blue Dye #1 | 0.1 |
| Denatonium Benzoate | 0.002 |
| Total | 100.0% |

To make the formulation, the technical propiconazole, which at room temperature is highly viscous or semi-solid, is heated to a temperature high enough, approximately 50° C., to melt the technical to a syrup-like consistency and eliminate all crystalline traces. The ethoxylated castor oil may also be heated to eliminate any phase differentiation and ensure fluidity. These ingredients, along with the clear, liquid tetrahydrofurfuryl alcohol, the dark powder dye and the denatonium benzoate in the form of small white pellets, are combined together in any order, to form a clear, blue, homogenous liquid formulation. The water is then added, preferably dropwise, to form the final concentrate formulation.

The formulation may be applied using microinjectors or macroinjectors. For use in microinjectors, the formulation need not be diluted.

The formulation is particularly useful as a root flare injection for prevention and treatment of oak wilt of oak and dutch elm disease of elms. These fungi infect the vascular system and cause plugging throughout the tree. The formulation is preferably injected into flare roots to ensure distribution throughout the vascular system of the tree.

Oak trees exhibiting less than 20% crown loss from oak wilt have the best chance of responding to treatment by the formulation. Preventive application is more effective than therapeutic treatment into trees showing disease symptoms. Trees in advanced stages of disease development may not respond to treatment.

Uninfected trees generally absorb the full amount of the formulation within one hour. Infected trees absorb the formulation more slowly due to the vascular plugging caused by the disease. If the formulation is not absorbed within 24 hours, the tree is considered high risk and has a poor chance of survival.

For treatment of oak wilt and Dutch elm disease, 10 ml. of the formulation of Example 1 is used per each inch DBH.

The formulation is non-phytotoxic to the cambium layer in trees.

The formulation of Example 1 is highly systemic and provides 95–100% control of tree diseases for prolonged periods of time. The fine particle size allows penetration throughout the entire tree. Also, being a microemulsion, there is no emulsion separation and agitation is not required to ensure a homogeneous mixture.

Comparative Example 1A

A macroemulsion concentrate formulation has the following ingredients:

| Ingredient | % by weight |
| --- | --- |
| Propiconazole Technical (91.7% active ingredient) | 15.6 |
| Tenneco T500-100 (xylem) | 80.4 |
| Ethoxylated Castor Oil (36–40 moles ethylene oxide) | 0.4 |
| Dodecyl Benzene Sulfonic Acid (DDBSA), Calcium Salt | 1.6 |
| White Oil (eye irritation mitigant) | 2.0 |
| Total | 100.0% |

Comparison

Example 1 and Comparative Example 1A each contain the same amount of active ingredient. The differences between Example 1 and Comparative Example 1A are set forth in Table 1:

TABLE 1

| Property | Example 1 | Comparative Example 1 |
| --- | --- | --- |
| Type of concentrate | microemulsion | macroemulsion |
| Ave. particle size upon dilution | 0.01–0.1μ | 1–3μ |
| Dilution needed | none | much |
| Appearance upon dilution | transparent | milky emulsion |
| Separation of emulsion over time | no | yes |
| Agitation necessary for homogeneity | no | yes |
| Absorption by tree | rapid (1–2 hours) | slow (12+ hours) |
| Injecter which can be used | micro or macro | macro only |
| Phytotoxicity | none | slight |
| Ratio of emulsifying agent to active ingr. | 2:1 | 1:40 |
| Solvent | water-miscible | not water-miscible |

EXAMPLE 2

Six to ten ml. of the formulation of Example 1 may be diluted with water to make a volume of one liter. The diluted formulation is then applied to the tree by macroinjection techniques. One liter of this diluted formulation per inch DBH is recommended.

If dilution is desired, it is recommended that the formulation of Example 1 not be diluted in the formulation:water ratio between 1:1 and 1:20. Dilutions outside this range, i.e. less than 1:1 and more than 1:20, are stable over a long period of time. However, the range between 1:1 and 1:20, particularly at approximately 1:13, is meta stable, and standing over a period of time begins to become cloudy.

EXAMPLE 3

A fungicidal microemulsion composition includes the following ingredients:

| Benomyl | 6% |
| --- | --- |
| γ-butyrolactone | 49% |
| Ethoxylated tallowamine (15 moles ethylene oxide) | 30% |
| water | 15% |

EXAMPLE 4

An insecticidal microemulsion composition includes the following ingredients:

| Diazinon | 7% |
| --- | --- |
| N-methylpyrrolidone | 40% |
| Ethoxylated castor oil (36–40 moles ethylene oxide) | 30% |
| water | 23% |

It will thus be seen that the objects set forth above, among those made apparent from the preceding description, are efficiently attained and, since certain changes may be made in carrying out the above composition and in the method set forth without departing from the spirit and scope of the invention, it is intended that all matter contained in the above description shall be interpreted as illustrative and not in a limiting sense.

It is also to be understood that the following claims are intended to cover all of the genetic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. An agrachemical microemulsion composition suitable for microinjection into trees without dilution, said composition comprising:

a) a nonpolar fungicide selected from the group consisting of non-polar triazoles, non-polar carbamates, non-polar acetanilides, and non-polar imidazoles having a particle size in the microemulsion of between about 0.01 and about 0.1 microns;

b) a water-miscible solvent which is present in an amount between about 0.5 to about 5 parts by weight per part of the fungicide; and c) an emulsifying agent which is present in an amount between about 0.2 to about 3 parts by weight per part of the fungicide.

2. The composition of claim 1, wherein stud solvent is present in an amount of about 3 parts by weight per part active ingredient.

3. The composition of claim 1, wherein said emulsifying agent is present in an amount of about 2 parts by weight per part active ingredient.

4. The composition of claim 1, wherein said active ingredient is a fungicide selected from the group consisting of propiconazole, hexaconazole, triadimefon, benoymyl, thiophanate-methyl, metalaxyl, oxadixyl, thiabendazole and carbendazim.

5. The composition of claim 1, wherein said water-miscible solvent is selected from the group consisting of alcohols, ketones, glycerine, glycols, glycol ethers and heterocyclic compounds.

6. The composition of claim 5, wherein said water-miscible solvent is selected from the group consisting of 1-butanol, 2-butanol, tetrahydrofurfuryl alcohol, methanol, acetone, propylene glycol, propylene glycol monoethyl ether, y-butyrolactone and n-methyl pyrrolidone.

7. The composition of claim 1, wherein said emulsifying agent is selected from the group consisting of alkoxylated alkyl amines, alkoxylated alkyl phenols, alkylphenyl sulfonate, alkylphenyl sulfonate metal salts, alkylphenyl sulfonate amine salts, dialkyl sulfosuccinates, alkoxylated natural oils, tetraalkyl ammonium salts, polyoxyalkylene copolymers, alkylated polyglycosides, alkylated saccharides and polysaccharides.

8. The composition of claim 1, wherein said composition further comprises an inert carrier.

9. The composition of claim 8, wherein said inert carrier includes water.

10. The composition of claim 8, wherein said inert carrier includes a dye.

11. A method of preventing damage to a tree or treating a tree against damage from disease, said method comprising applying a fungicidally-effective amount of the composition of claim 1 to the tree with a microinjector.

* * * * *